United States Patent [19]
Leu

[11] 3,971,135
[45] July 27, 1976

[54] DENTAL BUR

[75] Inventor: Robert F. Leu, Delta, Ohio

[73] Assignee: Dentsply Research & Development Corporation, Milford, Del.

[22] Filed: Sept. 4, 1975

[21] Appl. No.: 610,206

Related U.S. Application Data

[63] Continuation of Ser. No. 505,178, Sept. 11, 1974, abandoned.

[52] U.S. Cl. .................................................. 32/48
[51] Int. Cl.² ......................................... A61C 3/02
[58] Field of Search ............ 32/46, 48; 75/321, 421, 75/394

[56] References Cited
UNITED STATES PATENTS

| 683,696 | 4/1925 | Maillard | 32/48 |
| 1,211,537 | 1/1917 | Burton | 175/394 |
| 3,117,637 | 1/1964 | Mortensen | 175/394 |

Primary Examiner—Robert Peshock

[57] ABSTRACT

A helical dental bur having a shank provided on one end with a cutting head having a series of similar teeth extending longitudinally and spaced evenly around the circumference thereof; said teeth each having a flat cutting face extending from the cutting edge radially toward the axis of the head to form one side of said tooth and provide a positive cutting rake therefor, a relative deep chip gash adjacent said face, and a convex relief surface extending from the cutting edge toward said gash adjacent the next succeeding tooth to form the opposite side of each tooth, said convex relief surface permitting said chip gashes to be substantially deeper than such gashes in conventional burs without sacrificing strength of said teeth to resist chipping and breakage of said cutting edges, as well as including the benefit of said flat cutting face which extends radially to provide said positive cutting rake.

16 Claims, 7 Drawing Figures

DENTAL BUR

This is a continuation of application Ser. No. 505,178, filed Sept. 11, 1974 and now abandoned.

BACKGROUND OF THE INVENTION

This invention relates to dental burs and, more particularly, to dental burs of the type in which the cutting head is formed from carbide blanks which are fixedly connected to one end of stems or shanks formed from conventional steel for attachment to the chuck of a dental handpiece. The present invention more specifically pertains to the type of dental burs in which the burs are provided with a plurality of cutting teeth that extend longitudinally of the cutting head, each tooth being provided with a cutting edge spaced circumferentially even distances from adjacent cutting edges, said cutting edges being formed by grinding operations. When forming the cutting heads from carbide, diamond grinding wheels are conventionally used to form the edges by grinding operations.

The invention also pertains to dental burs in which the cutting edges are of the helical type. Dental burs of the type to which the present invention pertains are provided with a chip-receiving gash or groove adjacent one edge of each tooth and the opposite edge of the tooth is formed by a so-called relief surface which provides clearance immediately to the rear of the cutting edge of each tooth and thus, offer no resistance relative to the sidewall of a cavity, for example, which is being prepared in a tooth by the use of said bur.

One of the objectives of burs of this type which presently are in use is to provide a chip-receiving gash or groove having a depth adequate to accommodate chips removed from a tooth in which the bur is operating but, in order to provide a gash or groove of substantial depth, it is necessary at present to sacrifice some of the strength of the cutting edge which is afforded by the relief surface that backs up the cutting edge when rotating in operative direction. This is due to the fact that, in order to grind a relatively deep chip-receiving gash or groove, it is necessary to form a relatively steep relief surface which results in a sharper cutting edge than otherwise and, particularly when the bur is formed from carbide, which is quite brittle, the sharper cutting edge is more readily subject to chipping when encountering hard substances than if the cutting edge were less sharp and a larger angle extended between the opposite faces of the cutting edge. The foregoing phenomenon is particularly prevelant when carbide burs having helical teeth thereon are ground by means of formed or shaped grinding wheels operating, for example, about a fixed axis while the bur is rotated about its axis when being fed forwardly against the periphery of the grinding wheel during such axial rotation of the bur to provide the helical outline of the cutting teeth by simultaneously forming the cutting face and relief surface with a single cutter during a single pass along the blank to form each tooth. Under such circumstances, the grinding of cutting teeth on carbide burs has, historically, been achieved by the use of profile diamond grinding wheels of commercial type.

Also in regard to the grinding of carbide burs of the type referred to by the use of profile grinding wheels, especially in regard to making burs having helical teeth extending generally in axial direction of the bur, a certain amount of generation of the curved surface which forms both sides of each tooth is necessary and this generally results in the formation of a cutting face having a negative cutting rake on said surface as distinguished from a positive cutting rake which is more efficient than a negative rake, as well as a relief surface which has a lesser angle between the clearance surface and a plane perpendicular to the cutting face at the cutting edge of each tooth.

The foregoing deficiencies and undesirable characteristics of conventional carbide burs, which are manufactured at present by conventional techniques and are commonplace in the trade, are obviated by the present invention in which superior cutting teeth on a carbide type bur are provided having improved structural and operational characteristics which tapered fissure burs and on inverted cone burs, details of which are set forth in detail hereinafter.

SUMMARY OF THE INVENTION

It is the principal object of the present invention to provide a dental bur, especially a dental bur of the carbide type, which has a carbide head provided with a series of teeth helically extending axially thereon, each tooth having a relatively deep chip-receiving gash along a flat radially extending cutting face defining one side of each tooth and the opposite side of each tooth being defined by a relief surface which is convex in cross-section to provide substantial resistance to wear and chipping of the cutting edge.

Ancillary to the foregoing object, it is a further object of the present invention to arrange said flat cutting face on one side of each tooth so as to extend radially in a manner to provide a positive cutting rake but, due to the convex relief surface on the opposite side of each tooth, there is no sacrifice in the strength of each cutting blade, especially the resistance thereof to chipping, notwithstanding the fact that the chip-receiving gash is substantially deeper than similar gashes provided on conventional burs, the root surface of said chip-receiving gashes or grooves also being concave in cross-section and merging with said flat cutting face of each tooth a substantial distance radially inward from the cutting edge of each tooth to afford maximum cutting efficiency for said cutting faces which define one side of each tooth as aforesaid.

It is a further object to provide a cutting bur in which the teeth are of the helical type, the chip clearance gash or groove is formed by a grinding wheel as a first operation, and the relief surface is formed by a second grinding wheel in a second grinding operation, both of said surfaces being generated by the grinding wheel when forming such helical teeth.

It is a further object of the present invention to provide cutting teeth of the type described above in which the relief surface on each tooth meets the adjacent wall of the chip-receiving gash or groove along a blunt rounded ridge which extends longitudinally along and between each adjacent pair of cutting edges of the teeth, said arrangement permitting employment of a smaller radial relief angle than permitted normally in the grinding of straight tooth burs by profiled grinding members.

Still another object of the invention is to provide said flat cutting face on each tooth so as to be of substantial radial dimension of said surface which is between 20% and 30% of the radial dimension of the head, the optimum percentage being substantially 25% of said radial dimension.

Still another object of the invention is to define said convex relief surface of each tooth in cross-section by means of a radius extending substantially from the root of the chip clearance gash adjacent the diametrically opposite tooth of the cutting head.

Ancillary to the foregoing, it is another object of the invention to form said convex relief surface to extend at an angle from each cutting edge wherein the angle between the plane perpendicular to the flat cutting face of each tooth and a plane tangent to said relief surface at the cutting edge of each tooth is not substantially in excess of 30°.

Still another object of the invention is to form the helix angle of the teeth relative to the axis of the bur to be substantially between 10° and 30°, with an optimum helix angle of substantially 12°.

A still further object of the invention is to provide the cutting faces of the head, at the ends thereof opposite the shank end, with cutting points defined on one side by end grooves having concave root surfaces and extending radially toward the axis of the head in alignment with the ends of the chip-receiving gashes between said teeth and said end grooves extending at an acute angle to the cutting edges of the teeth, one sidewall of the end groove between each successive pair of teeth being nearly parallel to an axial plane extending along the axis of the head and intersecting the flat radial cutting face of each tooth to define a substantially stubby cutting tip at the intersection of said radial cutting face and relief surface of each tooth with said one sidewall of each end groove, and the other sidewall of said end grooves sloping gradually toward the cutting point of the next tooth to provide relief for said cutting points while providing substantial material mass circumferentially rearward of said cutting points relative to the direction of rotation of said bur.

Details of the foregoing objects and of the invention, as well as other objects thereof, are set forth in the following specification and illustrated in the accompanying drawings comprising a part thereof.

DETAILED DESCRIPTION

Figure 2:
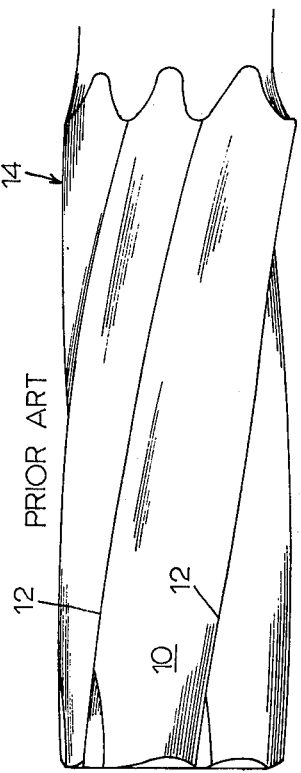
FIGS. 1 and 2 respectively show an outer end elevation and a side elevation of one type of dental bur of the prior art in which the teeth are of a helical type.
Figure 1:
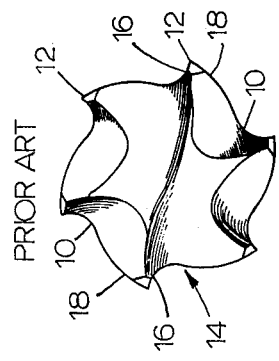

A typical type of conventional helical dental bur of the carbide type is illustrated in end view, in FIG. 1, and in fragmentary side elevation in FIG. 2, for purposes of contrasting certain characteristics thereof with the preferred construction of the dental bur comprising the subject matter of the present invention, a preferred embodiment of which is illustrated in FIGS. 3–7. As indicated above, in regard to grinding the helical flutes, grooves or chip-receiving gashes 10 to form the helical cutting edges 12, it is conventional to form said flutes, grooves or gashes by means of using a contoured diamond wheel which is operable about a substantially fixed axis extending transverse to the axis of the bur 14, and the bur is advanced to the grinding wheel while being rotated about the axis of the bur in order to form the helical cutting edges 12. As a result, the substantially concave flutes, grooves or gashes are substantially ogee in end view as is clearly evident from FIG. 1, due to said surface being generated by said profiled wheel. As a result, a number of deficiencies are produced, as follows:

Among the foregoing of such deficiencies and objectionable features are the facts that the cutting face 16, which extends along each tooth has a negative rake as distinguished from a positive rake as is clearly apparent from FIG. 1. Another deficiency is that the chip-receiving gashes 10 are only of limited depth because, if the same were to be provided with a greater depth, the relief surface 18 which defines the opposite side of each cutting edge 12 from the cutting face 16 would be at a sharper angle with respect to said cutting faces and thereby weaken the tooth and render the same more prone to chipping. As long as the compound chip-receiving gashes 10 and relief surfaces 18 are generated by a single grinding wheel when making a helical type bur, it is necessary to sacrifice strength in favor of depth of chip-receiving gash or vice versa.

Figure 5:
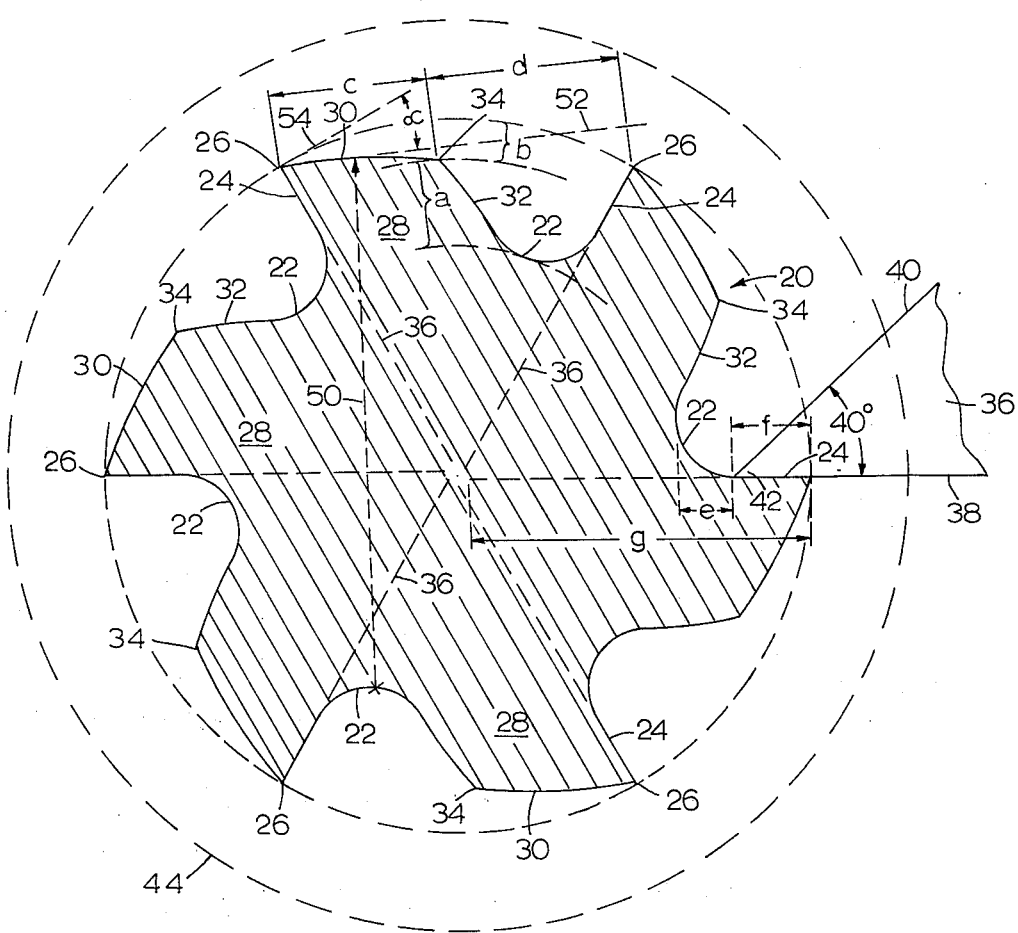
FIG. 5 is a transverse sectional view of the embodiment of improved dental bur illustrated in FIGS. 3 and 4 as seen on the line 5—5 of FIG. 4, said sectional view being on a substantially larger scale than employed in FIGS. 3 and 4 for purposes of showing numerous details of the shape of the cutting teeth of the bur and the surfaces which define the same.

In contract to the foregoing, the present invention provides a bur 20 which, particularly by reference to FIG. 5, will be seen to have a chip-receiving groove or gash 22 which is of a much greater depth in a radial direction than in the conventional bur shown in FIG. 1 and is defined along one side by a radially extending flat cutting face 24 which defines one side of the cutting edge 26 of each tooth 28. The opposite surface of each cutting edge 26 is defined by a relief surface 30 which is convex in cross-section and merges with the adjacent side surface 32 of the chip-receiving gash 22 along a blunt, rounded ridge 34 which extends longitudinally along the head of the bur 20. The preferred location of the ridge 34 is approximately midway between the successive cutting edges 26 but other locations thereof within reasonable limits are possible. Further, it will be seen that the edge of the concave groove or gash 22 which merges with the flat cutting face 24 in no way interferes with the radial disposition of the face 24 of substantial radial dimension which provides a positive cutting rake, as clearly illustrated by the dotted line 36 comprising projections of said cutting faces 24 radially inward toward the axis of the head of the bur. Forming the compound surface of 22 and 30 which meet along the blunt rounded ridge 34 is best achieved in connection with the forming of helical teeth having helical cutting edges 26. This is due to the fact that the full contour of each tooth 28 readily is formed by generation resulting from the use of a diamond wheel 36, a fragmentary portion of the edge of which is illustrated in FIG. 5 relative to the gash 22.

Figure 4:
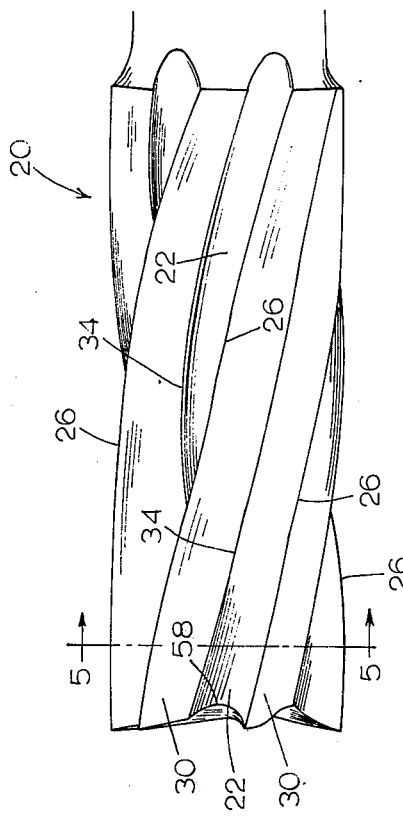
FIG. 4 is a fragmentary elevation comprising a side view of the dental bur illustrated in FIG. 3, and in which the longitudinal teeth are of the helical type.

It will be seen that the preferred type of diamond wheel 36 has a flat face 38 and a beveled edge 40 resulting in a sharp peripheral edge 42. The wheel 36 rotates about an axis extending transverse to the axis of the bur 20 and is fixed relative to the machine which supports and operates it. In the preferred operation of the machine in which the burs 20 are formed, the blank burs have a cylindrical outer surface 44 on the head thereof, as shown in outline in FIGS. 5 and 7. In making the initial grinding cut for each tooth, the flat cutting face 24 thereof is continuously formed along one side of each tooth by the sharp peripheral edge 42 of the diamond wheel 36 and the flat face 38 thereof. Rotation of the bur blank about its axis and axial feed is effected by the machine on which it is formed. The helix angle of the teeth with respect to the axis of the bur, as illustrated in FIG. 4, is approximately 12°, which is the preferred optimum angle. However, said helix angle may vary within a range of between 10° and 30° within the spirit of the present invention.

Figure 7:
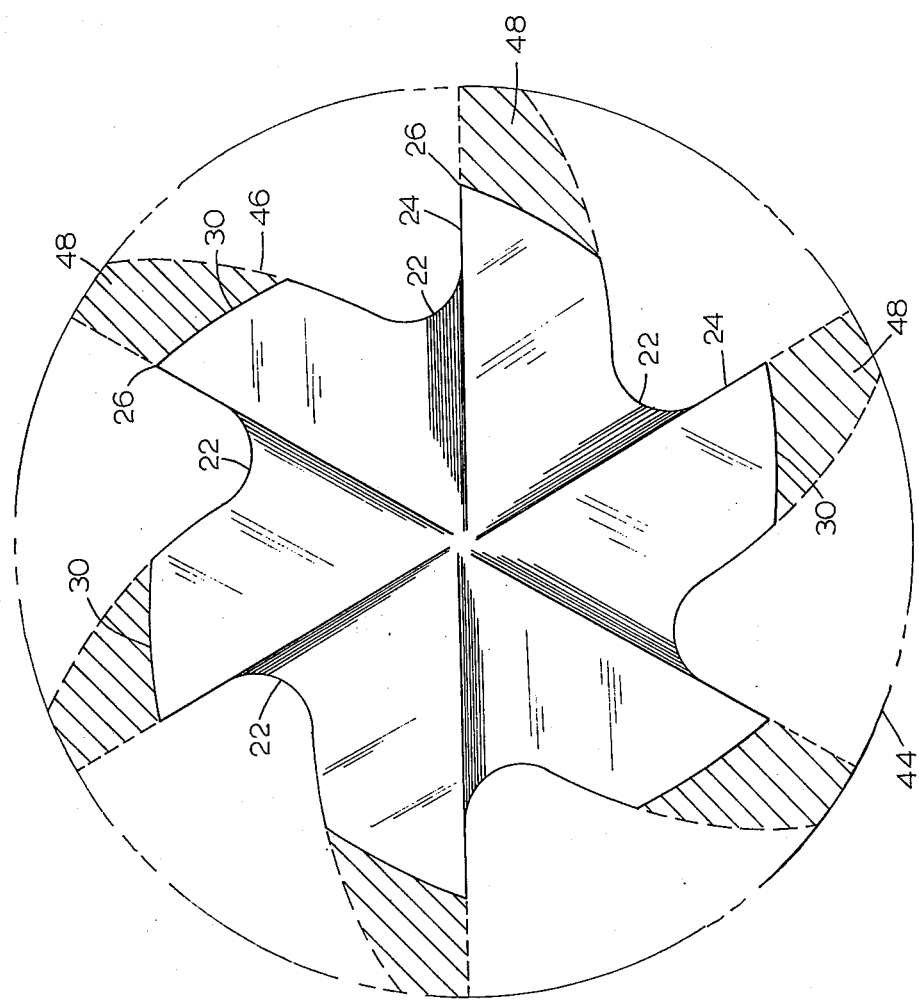
FIG. 7 is a view similar to FIG. 5 but being diagrammatic for purposes of illustrating details of the manner in which the preferred embodiment of the dental bur shown in FIGS. 3-6 is formed by the preferred processes described hereinafter for grinding said bur from a bur blank.

As the bur blank is rotated about its axis and axially fed, the concave root surface of each groove or gash 22, as clearly shown best in FIGS. 5 and 7 in enlarged detail, is generated and said initial cut to form said chip-receiving grooves or gashes 22 is defined on one side by the cutting face 24, shown in FIG. 7, and on the opposite side by the slightly convex outline 46, which is best shown in FIG. 7. The bur blank is indexed one aliquote space after each initial cut has been made and the next successive initial cut is formed in the blank until all of the initial cuts have been made by the grinding action of the diamond wheel 36 to form the gashes 22.

The bur then preferably is advanced to another station on the grinding machine where another diamond wheel, not shown, but preferably similar to the wheel 36, progressively forms the relief surfaces 30 by removing additional amounts of material 48 from the bur blanks, as shown by the cross-hatched illustration thereof in FIG. 7. The removal of the additional amounts of material 48 by said diamond wheel preferably is accomplished by the wheel rotating in a direction by which the grinding is accomplished from the cutting edges 26 toward the gashes 22. As a result, this is a sharpening cut and no final or additional finishing operations for the cutting edges 26 are required, thereby minimizing the cost of production of such burs. Such final grind or cut is made preferably by a finer grit diamond grinding wheel to insure against any ragged edge being formed since smooth cutting edges afford the longest life in carbide burs.

The relief surfaces 30 described above comprise an arc generated by a radius extending substantially from the root of the gash of the diametrically opposite tooth on the bur, as indicated by the dotted radius line 50. As also described above, this relief surface joins the side edge of the gash 22, which is opposite the flat cutting face 24, along a blunt, rounded ridge 34. This provides adequate relief rearward of the cutting edges 26 of the teeth without sacrificing strength, while at the same time providing a chip-receiving gash 22 of substantial depth and, in general, having a much greater radial dimension than any chip-receiving gashes in conventional dental burs.

In conventional burs, the clearance surface rearward of the cutting edges is coincident with a straight edge extending between adjacent cutting teeth. From FIG. 5, it will be seen that the tangent line 52 is above the next adjacent cutting edge 26, thus providing a stronger relief surface 30 to permit the cutting edge to resist chipping or other damage.

Further, according to the present invention, the angle between the tangent line 52 and line 54 which is perpendicular to the flat cutting face 24, at the cutting edge 26 of the tooth, is approximately 24° but this is stated for purposes of being exemplary rather than restrictive. Further, the radial dimension of the blunt rounded ridge 34 relative to the cutting edge 26 of each tooth should always be less than the radial dimension between the root of the gash 22 and the blunt rounded ridge 34. In FIG. 5, the latter dimension is indicated by a bracket labeled $a$ and the former is indicated by a bracket labeled $b$.

Another preferred characteristic of the chip-receiving groove or gash 22 is that, as illustrated near the right-hand side of FIG. 5, the additional radial dimension of the actual bottom of the gash 22 beyond the inner edge of the flat cutting face 24 preferably is between 40% and 60% of the radial dimension of the flat cutting face. Said additional radial dimension of the innermost surface of gash 22 is indicated $e$ and the radial dimension of the flat cutting face is indicated by $f$. In accordance with the present invention, it is preferred that the radial dimension of the flat cutting face $f$ should be within a range between 20% and 30% of the radius $g$ of the cutting head of the bur, all of which dimensions are illustrated in FIG. 5.

The shape of the cutting teeth 28, as illustrated in FIGS. 3–7 and as described above is such as to provide ample relief clearance rearwardly of the cutting edges 26 of the teeth while, nevertheless, affording adequate backup mass of the material from which the head of the bur is formed so as to resist undue wear and especially the possibility of chipping the cutting edge due to the stubby nature of the cutting teeth in cross-section adjacent the cutting edge and this stubby configuration is present for substantially half of the radial width of the teeth between successive cutting edges before the adjacent sides of the chip-receiving grooves or gashes 22 commence to extend radially inward at a greater rate than the clearance surfaces 30 in order to provide chip-receiving grooves or gashes 22 of very substantial depth and fully adequate to accommodate the chips resulting from operation of the burs in the preparation of tooth structure for restorative purposes. Such grooves or gashes 22 also are provided in a manner which in no way interferes with the flat radial cutting faces 24 which provide positive cutting rakes for each tooth without sacrificing strength thereof, while at the same time providing very substantial resistance to chipping of the cutting edges 26.

Figure 3:
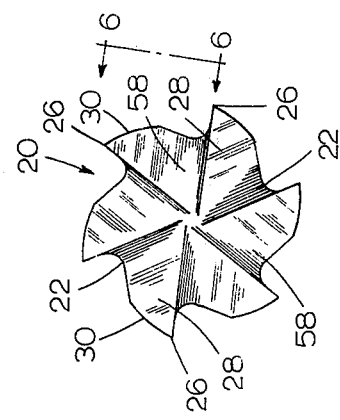
FIG. 3 is an outer end view of a dental bur comprising the preferred embodiment of the present invention, said view showing the cutting tips at the outer end of the bur, as well as the outline of the cutting teeth which extend longitudinally of the bur.
Figure 6:
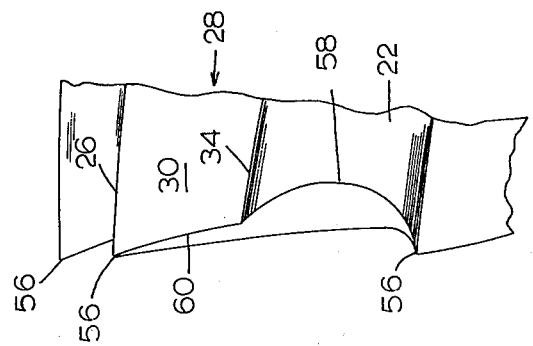
FIG. 6 is a fragmentary end elevation of a portion of the outer end of the dental bur shown in FIG. 3, as seen on the line 6—6 thereof for purposes of illustrating the details of the cutting tips at the outer end of each cutting blade, the scale employed in FIG. 6 being substantially larger than that in FIG. 3.

The present invention also provides improvements for the outer ends of the bur, especially the cutting tips 56 which respectively are formed at the outer end of each cutting edge 26, as best shown in FIG. 6. Referring also to FIG. 3, it will be seen that each cutting tip 56 is formed by grinding a radial groove 58, shown in end view in FIG. 3, but also illustrated in side elevation in FIG. 6 with respect to a single tooth 28. The radial groove also extends from the outer ends of the chip-receiving gashes 22, inward toward the axis of the bur at an acute angle to the cutting edges 26 of the teeth. Said grooves preferably are formed by a cutting wheel of the diamond type similar to wheel 36 which operates to generate the groove 58, as the bur is rotated slowly about its axis and, by the time the cutting wheel reaches the portion of each tooth on which the relief surface 30 occurs, a more gradually sloping outer end surface 60 is formed by the cutting wheel. Such configuration results in backing up the cutting tips 56 for strength and resistance to chipping, while at the same time, providing adequate clearance surfaces for chips.

While the invention has been described and illustrated in its several preferred embodiments, it should be understood that the invention is not to be limited to the precise details herein illustrated and described since the same may be carried out in other ways falling within the scope of the invention as illustrated and described.

I claim:

1. A helical dental bur comprising a shank and a head fixed to one end thereof, said head being provided with a plurality of similar teeth extending longitudinally therealong and having a sturdy sharp cutting edge outermost thereon, each of said teeth having a flat cutting face extending from the cutting edge radially toward the axis of the head, a relief surface which is convex in cross-section extending from said cutting edge partially toward the cutting face of the next succeeding tooth, and a chip-receiving gash having a concave surface in cross-section which extends between said relief surface and said flat cutting face, thereby to provide teeth on a dental bur which have a positive cutting rake afforded by said flat cutting face and a cutting edge rendered strong by said convex relief surface, in combination with a relatively deep chip gash adjacent said flat cutting face without sacrificing strength for the cutting edge of each tooth.

2. The dental bur according to claim 1 in which said relief surface and gash provide substantially an ogee surface in transverse cross-section, one edge of such surface abutting said flat radial face in radially spaced relationship with respect to the cutting edge of each tooth.

3. The dental bur according to claim 1 in which said relief surface and adjacent edge of the gash adjacent each tooth meet along a bluntly rounded ridge extending longitudinally of said head between each pair of adjacent cutting edges of the teeth.

4. The dental bur according to claim 3 in which said bluntly rounded ridge is substantially circumferentially midway between said cutting edges of adjacent teeth and radially is at a level farther from the root of the gash than from the cutting edge of each tooth.

5. The dental bur according to claim 1 in which the edge of the gash adjacent each flat cutting face engages said face within a range between 20% and 30% of the radius of said head, measured from the circumference.

6. The dental bur according to claim 1 in which the edge of the gash adjacent the flat cutting face of each tooth engages the same at approximately 25% of the radius of the head, measured from the circumference.

7. The dental bur according to claim 5 in which the root surface of each gash extends radially a distance within the range between 40% and 60% of the radial length of the flat cutting face of each tooth.

8. The dental bur according to claim 5 in which the convex relief surface of each tooth in cross-section has a radius extending substantially from the root of the gash of the diametrically opposite tooth to the cutting edge of each tooth.

9. The dental bur according to claim 8 in which the angle between a plane perpendicular to the flat cutting face of each tooth and a plane tangent to the relief surface at the cutting edge of each tooth is not substantially in excess of 30°.

10. The dental bur according to claim 1 in which said helical cutting teeth have convex relief surfaces generated by a grinding wheel having edges acutely angular in cross-section, whereby said convex generation results from the rotation and axial feed of said bur relative to a grinding wheel rotating about a fixed axis extending transversely to the axis of said bur.

11. The dental bur according to claim 10 in which the helix angle of said teeth relative to the axis of said bur is between substantially 10° and 30°.

12. The dental bur according to claim 10 in which said helix angle between the teeth and the axis of the bur is substantially 12°.

13. The dental bur according to claim 10 in which the gash adjacent each tooth has a root which is concave in cross-section and generated by a grinding wheel having an edge acutely angular in cross-section and said concave generation resulting from the axial feed and rotation of the bur about its axis relative to the grinding wheel rotating about a fixed axis transverse to the axis of the bur.

14. The dental bur according to claim 10 in which the wall of each gash opposite the radial cutting face of each tooth is slightly convex in cross-section, and said convex relief surface extending from the cutting edge of each tooth is produced by a second grinding operation which produces said bluntly rounded ridge which extends longitudinally between adjacent teeth.

15. The dental bur according to claim 14 in which said bluntly rounded ridge is substantially midway circumferentially between the cutting edges of successive teeth.

16. The dental bur according to claim 1 in which the ends of the teeth opposite the shank end of the head terminate in cutting points respectively defined on one side by end grooves formed in the outer end of said head and having concave root surfaces extending radially toward the axis of said head in alignment with the ends of said chip-receiving gashes extending along one side of each tooth, one sidewall of said end grooves extending nearly parallel to an axial plane intersecting in parallel to the axis of the head and within which the flat radial cutting face of each tooth extends to define a substantially stubby cutting tip at the intersection of said radial cutting face and relief surface of each tooth with said one sidewall of each end groove, and the outer sidewall of said end groove sloping gradually toward the cutting point of the next tooth to provide a relief surface for said cutting point while providing substantial material mass circumferentially rearward of said cutting point relative to the direction of rotation of said bur.

* * * * *